US007885770B2

(12) United States Patent
Gill et al.

(10) Patent No.: US 7,885,770 B2
(45) Date of Patent: Feb. 8, 2011

(54) METHODS FOR SETTING UP, MONITORING AND PERFORMING ANALYSIS USING CAPILLARY GEL ARRAYS

(75) Inventors: Peter Gill, Birmingham (GB); Peter Koumi, Birmingham (GB); Kam Tsang, Birmingham (GB)

(73) Assignee: The Secretary of State for the Home Department c/o The Forensic Science Service, Birmingham (GB)

( * ) Notice: Subject to any disclaimer, the term of this patent is extended or adjusted under 35 U.S.C. 154(b) by 1339 days.

(21) Appl. No.: 10/486,870

(22) PCT Filed: Aug. 15, 2002

(86) PCT No.: PCT/GB02/03765

§ 371 (c)(1),
(2), (4) Date: May 13, 2004

(87) PCT Pub. No.: WO03/016566

PCT Pub. Date: Feb. 27, 2003

(65) Prior Publication Data

US 2004/0197925 A1    Oct. 7, 2004

(30) Foreign Application Priority Data

Aug. 16, 2001    (GB) .................................. 0119959.5

(51) Int. Cl.
*G06F 19/00* (2006.01)
(52) U.S. Cl. ........................................................ 702/20
(58) Field of Classification Search .................... 702/20
See application file for complete search history.

(56) References Cited

U.S. PATENT DOCUMENTS 5,332,481 A * 7/1994 Guttman ..................... 204/455

FOREIGN PATENT DOCUMENTS

WO    WO 99/45148    9/1999

OTHER PUBLICATIONS

Zhang et al., Analytical Chemistry, vol. 68, pp. 2927-2931, 1996.*
Nock et al., Electrophoresis, vol. 22, pp. 755-762, 2001.*
Lazaruk et al. Electrophoresis, vol. 19, pp. 86-93, 1998.*
Mansfield E. S. et al.: "Sensitivity, reproducibility, and accuracy in short tandem repeat genotyping using capillary array electrophoreses." *Genome Research*. United States Sep. 1996., Sep. 1996, vol. 6, No. 9, pp. 893-903, XP009018591.
Vainer M. et al.: "Short Tandem Repeat Typing by Capillary Array Electrophoresis: Comparison of Sizing Accuracy and Precision Using Different Buffer Systems." *Genomics, Academic Press*, San Diego, US, Jan. 4, 1997, vol. 41, No. 1,pp. 1-9, XP000901000.
Wooley A. T. et al.: "High-Speed DNA Genotyping Using Microfabricated Capillary Array Electrophoresis Chips." *Analytical Chemistry*, American Chemical Society, Columbus, US, vol. 69, No. 11, Jun. 1, 1997, pp. 2181-2186, XP000696550.
Mansfiled E. S. et al.: "Rapid Sizing of Polymorphic Microsatellite Markers by Capillary Array Electrophoresis." *Journal of Chromatography A. Elsevier Science, NL*, vol. 781, No. 1-2, 26, Sep. 1997, pp. 295-305, XP004094560.
Mansfield E. S. et al.: "Analysis of multiplexed Short Tandem Repeat (STR) Systems Using Capillary Array Electrophoresis." *Electrophoresis, Wienheim, DE*, vol. 19, No. 1, 1998, pp. 101-107, XP000893179.
International Search Report (Oct. 17, 2003).
Gill et al., "A new method of STR interpretation using inferential logic—development of a criminal intelligence database," *Int. J. Legal Med.* (1996) 109: 14-22.
Elder et al., "Measurement of DNA length by gel electrophoresis II: Comparison of methods for relating mobility to fragment length," *Analytical Biochemistry* (1983) 128: 227-231.
Greenspoon et al., "QIAamp spin columns as a method of DNA isolation for forensic casework," *J. Forensic Sci.* (1998) 43: 1024-1030.
Cotton et al., "Validation of the AMPFlSTR® SGM Plus™ system for use in forensic casework," *Forensic Science International* (2000) 112: 151-161.

* cited by examiner

*Primary Examiner*—Jerry Lin
(74) *Attorney, Agent, or Firm*—Merchant & Gould P.C.

(57)    ABSTRACT

Set up methods, analysis methods and monitoring methods for capillary gel arrays are provided which rigorously determine the number of capillaries for which standards should be used and/or the capillaries in which standards should not be considered and/or for which performance is impaired. The invention includes methods for monitoring capillary gel array performance in which the capillary gel array performs, on a plurality of occasions, a size based separation on an unknown sample in one or more capillaries, a size based separation on a second standard in those one or more capillaries, and a size based separation on a standard in one or more other capillaries, comprising comparing the results of the sample to the results of the standards in which variation in a characteristic of the results from the capillaries provided with the standard are considered with time and variation of the characteristic outside a predetermined position to determine if one or more of the capillaries of the array are providing reduced performance. The invention provides rigour to the results obtained from capillary gel array analysis and prevents analysis being carried out on arrays which have developed problems or broken down.

12 Claims, 5 Drawing Sheets

Table 1 : A comparison of standard deviations for HUMFIBRA alleles across five different arrays

| FGA allele | mean size (bases) | Standard deviation | | | | |
|---|---|---|---|---|---|---|
| | | 1 | 2 | 3 | 4 | 5 |
| 17 | 214.21 | 0.102 | 0.090 | 0.103 | 0.102 | 0.095 |
| 18 | 218.21 | 0.106 | 0.090 | 0.101 | 0.103 | 0.098 |
| 19 | 222.30 | 0.110 | 0.102 | 0.105 | 0.110 | 0.100 |
| 20 | 226.47 | 0.114 | 0.104 | 0.114 | 0.112 | 0.108 |
| 21 | 230.62 | 0.115 | 0.108 | 0.125 | 0.116 | 0.113 |
| 22 | 234.76 | 0.114 | 0.108 | 0.127 | 0.111 | 0.110 |
| 23 | 238.93 | 0.117 | 0.107 | 0.140 | 0.109 | 0.114 |
| 24 | 243.08 | 0.116 | 0.109 | 0.132 | 0.105 | 0.111 |
| 25 | 247.16 | 0.115 | 0.108 | 0.122 | 0.101 | 0.106 |
| 26 | 251.21 | 0.118 | 0.106 | 0.112 | 0.107 | 0.111 |
| 26.2 | 253.22 | 0.113 | 0.109 | 0.109 | 0.104 | 0.105 |
| 27 | 255.21 | 0.119 | 0.109 | 0.108 | 0.112 | 0.104 |
| 28 | 259.23 | 0.118 | 0.111 | 0.105 | 0.106 | 0.105 |
| 29 | 263.23 | 0.114 | 0.109 | 0.109 | 0.110 | 0.108 |
| 30 | 267.25 | 0.122 | 0.109 | 0.112 | 0.119 | 0.107 |
| 30.2 | 269.07 | 0.119 | 0.117 | 0.117 | 0.111 | 0.111 |
| 31.2 | 273.08 | 0.127 | 0.117 | 0.121 | 0.114 | 0.114 |
| 32.2 | 277.08 | 0.126 | 0.123 | 0.127 | 0.114 | 0.108 |
| 33.2 | 281.10 | 0.134 | 0.120 | 0.138 | 0.123 | 0.118 |
| 42.2 | 317.93 | 0.145 | 0.125 | 0.129 | 0.131 | 0.134 |
| 43.2 | 322.04 | 0.145 | 0.123 | 0.139 | 0.130 | 0.129 |
| 44.2 | 326.13 | 0.153 | 0.134 | 0.136 | 0.129 | 0.132 |
| 45.2 | 330.23 | 0.145 | 0.128 | 0.136 | 0.141 | 0.129 |
| 46.2 | 334.25 | 0.147 | 0.129 | 0.148 | 0.145 | 0.154 |
| 47.2 | 338.32 | 0.156 | 0.136 | 0.147 | 0.150 | 0.142 |
| 48.2 | 342.43 | 0.154 | 0.131 | 0.147 | 0.156 | 0.133 |
| 50.2 | 350.56 | 0.151 | 0.141 | 0.149 | 0.147 | 0.133 |
| 51.2 | 354.57 | 0.160 | 0.136 | 0.152 | 0.148 | 0.147 |

FIG. 4

METHODS FOR SETTING UP, MONITORING AND PERFORMING ANALYSIS USING CAPILLARY GEL ARRAYS

This invention concerns improvements in and relating to analysis, in particular, but not exclusively, in relation to capillary array gel electrophoresis.

Capillary array gel electrophoresis is increasingly used in a variety of DNA analysis techniques. It is becoming more commonly used in short tandem repeat, STR, analysis due to its suitability for analysis of large numbers of samples in automated processes. STR analysis finds particular use in medical and forensic applications due to its ability to determine variations in the DNA of individuals. In forensic science it is used to establish profiles for individuals which can be compared with other profiles to establish a match or eliminate a match. The comparison may be with another sample or with established records of STR profiles for individuals.

Whilst capillary array gel electrophoresis is finding increasing use the applicant has established that there are a number of issues which could compromise the actual accuracy of the results or the validity of those results particularly in legal proceedings. Any question mark over the validity of a DNA profile or its comparison could be exploited in legal proceedings to question its evidential value. The present invention has amongst its aims the provision of results which are not subject to these issues.

The performance of capillary array gels with time can also vary and even breakdown, leading to wasted tests being performed before such problems are realised. The present invention has amongst its aims the monitoring of performance of arrays with time and the provision of warnings in advance of breakdown.

According to a first aspect of the invention we provide a method for setting up a capillary gel array for analysis use, in analysis use the capillary gel array performing a size based separation on an unknown sample in one or more capillaries and a size based separation on a standard in a number of other capillaries, the results of the one or more unknown samples being compared with the results from the one or more standards to obtain the analysis results, which set up method determines the number of capillaries in which the size based separation on a standard should be performed in analysis use, the set up method including, for one or more components of the standard:

determining a target standard deviation of the mean size for the component;

determining, by multiple size based set up separations, a relationship between the experimental standard deviation of the mean size for the component and the number of capillaries used for size based separations of the standard; and with the experimental standard deviation equating to the target standard deviation indicating, by means of the relationship, a boundary number of capillaries, the number of capillaries being used for size based separation of the standard in analysis use being a whole number and at least as great as the boundary number.

Preferably the set up method is used before any analysis use of the array. Preferably a set up method may be used for each array used on an instrument. The set up may be employed when the standard being used in the analysis method is changed.

Preferably the determination is of the minimum number of capillaries which should be used for size separation of standards, ideally whilst being statistically reliable to a given degree of confidence. Preferably the minimum number is used in the analysis use, ideally with all other capillaries being provided with unknowns.

The set up method may be performed on only one component of the standard. The components may be include a component of the heaviest weight loci present in the standard. The component may be or include the heaviest weight component of the standard, ideally the heaviest weight component of the heaviest weight loci present in the standard. The one component may be or include a component of the most AT rich loci present in the standard. The one component may be or may include the most AT rich component of the standard. The most AT rich may be the component with the most AT bases in total and/or the component with the highest proportion of AT bases in its sequence.

Preferably the one or more components includes the component with the highest standard deviation of mean size in experimental measurements of its size, particularly capillary gel electrophoresis measurements.

The target standard deviation may be based on one or more factors. The factors may include the tolerable discrepancy between the actual mean and experimentally determined mean size for that component and/or the degree of confidence required and/or the distribution type allocated to the allele size experimentally determined. The tolerable discrepancy is preferably +/−0.25 bases. The degree of confidence is preferably at least 95%, more preferably at least 98% and ideally at least 99%. The distribution type is preferably a normal distribution, but others may be provided.

The target standard deviation is preferably less than 0.1, more preferably less than 0.09 and ideally less than 0.083, particularly for a 96 capillary array and/or a normal distribution and/or a degree of confidence of 99% and/or a tolerance of +/−0.25 bases.

The target standard deviation and/or tolerable discrepancy and/or distribution type and/or degree of confidence may be different for different standards and/or numbers of capillaries in the array.

Preferably a plurality of set up size based separations are conducted for a component with a given number of capillaries provided with standard. Preferably the plurality is at least 25 times, more preferably at least 100 times, still more preferably at least 250 times and ideally at least 1000 times for each number of capillaries provided with the standard. Preferably a plurality of set up based size separations are provided for each of between 1 and 5, more preferably each of between 1 and 10 and ideally each of between 1 and 20 capillaries provided with the standard.

Preferably the relationship is the variation of standard deviation of the mean size of the component, experimental, with the number of capillaries provided with the standard.

Preferably the an experimental standard deviation value equivalent to the target standard deviation value is taken and applied to the relationship. Preferably the application of the experimental standard deviation relates to a number of capillaries provided with standard. Where the number is a whole number preferably that number of capillaries are provided with standard in the analysis use. Where the number is a non-whole number, preferably that number is rounded up to give the number of capillaries provided with the standard in analysis use.

The number is preferably a number between 2 and 6, more preferably between 3 and 5, still more preferably 4 or 5 ideally 4, particularly for the Applied Biosystems AMPFlSTR SGM PLUS system DNA profiling technique and/or HUMFIBRA locus and/or a 96 capillary array. Other numbers may arise for other multiplex systems for analysing STRs.

According to a second aspect of the invention we provide a method of analysis DNA in a sample using a capillary gel array, the use the capillary gel array performing a size based separation on an unknown sample in one or more capillaries and a size based separation on a standard in a number of other capillaries, the results of the one or more unknown samples being compared with the results from the one or more standards to obtain the analysis results, the set up method for which includes determining the number of capillaries in which the size based separation on a standard should be performed in analysis use, the set up method including, for one or more components of the standard:

determining a target standard deviation of the mean size for the component;

determining, by multiple size based set up separations, a relationship between the experimental standard deviation of the mean size for the component and the number of capillaries used for size based separations of the standard; and with the experimental standard deviation equating to the target standard deviation indicating, by means of the relationship, a boundary number of capillaries, the number of capillaries being used for size based separation of the standard in analysis use being a whole number and at least as great as the boundary number.

The second aspect of the invention may include any of the features, options or possibilities set out elsewhere in this document, with particular reference to those set out in the first aspect of the invention and related statements.

According to a third aspect of the invention we provide a method for setting up a capillary gel array for analysis use, in analysis use the capillary gel array performing a size based separation on an unknown sample in one or more capillaries and a size based separation on a standard in one or more other capillaries, the results of the one or more unknown samples being compared with the results from the one or more standards, in which set up method a group of capillaries at one or both ends of the array are excluded from use as capillaries for the standard in subsequent use of the array.

Preferably a group of capillaries from both ends of the array are excluded. The group of capillaries may be sequential in terms of the capillaries which are excluded. Preferably at least the first capillary or the last capillary of the array is excluded and ideally both.

One or both groups may include at least two or more preferably at least three capillaries. One or both groups may include between 2 and 4 capillaries in them and more preferably include three capillaries.

Preferably the excluded capillaries are used in analysis use for unknown samples.

The excluded capillaries may be additional to those excluded according to the method of the fifth aspect of the invention or may include one or more common capillaries.

Preferably a set up method of this type is performed on each array and/or each capillary array instrument before analysis use.

According to a fourth aspect of the invention we provide a method of analysing DNA containing samples using capillary gel arrays in which the capillary gel array performs a size based separation on an unknown sample in one or more capillaries and a size based separation on a standard in one or more other capillaries, the results of the one or more unknown samples being compared with the results from the one or more standards to provide the analysis results, in which set up method a group of capillaries at one or both ends of the array are excluded from use as capillaries for the standard in subsequent use of the array.

The fourth aspect of the invention may include any of the features, options or possibilities set out elsewhere in this document, with particular reference to those set out in the third aspect of the invention and related statements.

According to a fifth aspect of the invention we provide a method for setting up a capillary gel array for analysis use, in analysis use the capillary gel array performing a size based separation on an unknown sample in one or more capillaries and a size based separation on a standard in one or more other capillaries, the results of the one or more unknown samples being compared with the results from the one or more standards, in which a size based separation is performed in each of a plurality of the capillaries on a known material to determine a speed of migration related characteristic of the known material in those plurality of capillaries, those capillaries from amongst the plurality of capillaries which have a characteristic value outside a predetermined range being excluded from use as capillaries for the standard in subsequent use of the array.

Preferably the size based analysis of the set up method is performed on all the capillaries of the array. Preferably the same known material is used in each capillary. Preferably the characteristic value is determined by the distance the material has migrated in each of the capillaries in the same time period. The characteristic may be a speed of migration and/or a distance of migration and/or a size associated with that degree of migration. The size may be expressed in terms of bases.

The predetermined range may be defined by an upper limit. The predetermined range may be defined by a lower limit. The limits may be defined in absolute terms. The absolute terms may be exclude the highest few and/or lowest few characteristic values. The few may be one, two or even three in each case. The limits may be defined relative to a standard value, for instance the mean or median value. The relative definition may be provided as a +/−%. A range of +/−0.1% may be applied or a range of +/−0.075% may be applied, as the limit of the range, particularly when expressing the characteristic as relative sizes in terms of bases. The relative definition may be provided as a standard deviation relative to a standard value.

Preferably the excluded capillaries are used in analysis use for unknown samples.

The excluded capillaries may be additional to those excluded according to the method of the second aspect of the invention or may include one or more common capillaries.

Preferably a set up method of this type is performed on each array prior to analysis use.

If a characteristic is outside a further predetermined range, then the capillary may be excluded from use as capillaries for an unknown sample in subsequent use of the array. The further predetermined range may be a range of +/−0.5%, may more preferably be a range of +/−0.25% and may be a range of +/−0.15%, as the limit of the range, particularly when expressing the characteristic of relative sizes in terms in bases. The further predetermined range may be +/−5% of the distance of migration and/or speed of migration compared to the mean.

According to a sixth aspect of the invention we provide a method of analysing DNA containing samples using capillary gel arrays in which the capillary gel array performs a size based separation on an unknown sample in one or more capillaries and a size based separation on a standard in one or more other capillaries, the results of the one or more unknown samples being compared with the results from the one or more standards to provide the analysis results, and in which a size based separation is performed in each of a plurality of the capillaries on a known material to determine a speed of migration related characteristic of the known material in those plurality of capillaries, those capillaries from amongst the plurality of capillaries which have a characteristic value outside a predetermined range being excluded from use as capillaries for the standard in subsequent use of the array.

The sixth aspect of the invention may include any of the features, options or possibilities set out elsewhere in this document, with particular reference to those set out in the fifth aspect of the invention and related statements.

According to a seventh aspect of the invention we provide a method of monitoring capillary gel array performance in which the capillary gel array performs, on a plurality of occasions, a size based separation on an unknown sample in one or more capillaries and a size based separation on a standard in one or more other capillaries, the results of the one or more unknown samples being compared with the results from the one or more standards, in which variation in a characteristic of the standard results is considered with time and variation of that characteristic outside a predetermined position provides information on the array.

The performance may be the reliability of the results. The performance may be the migration speed of a standard in a capillary with time.

The plurality of occasions may be greater than 10 occasions, more preferably greater than 50 occasions, still more preferably greater than 100 occasions and even greater than 1000 occasions.

The characteristic may be the distance of migration of one or more components of the standard. The characteristic may be the speed of migration of one or more components of the standard. Preferably the characteristic is a standard deviation. The standard deviation may be of the speed of migration and/or distance of migration and/or more preferably the size of component, for one or more components of the standard.

The variation may be a change in the characteristic, particularly a change which causes the characteristic to cross a threshold. The threshold may be of an absolute value, for instance a preset speed, a preset distance or a preset standard deviation. The threshold may be a relative value.

The variation may be a change in the rate of variation of the characteristic, particularly a rate of change which exceeds a threshold. The threshold may be absolute or relative.

The variation may be determined after an occasion of use. The variation may be determined after each occasion of use or more preferably periodically. The variation may be determined from the results arising from the use. In particular the variation may be determined from the results for the standard obtained from one or more of the capillaries of the array, most preferably those standards being used in the comparison with the unknown samples in the occasion. The variation may be determined from a separate set of results to those arising from the occasions of use. In particular the separate set of results maybe obtained by running the array with the standards in one or more capillaries of the array, ideally specifically for the purpose of monitoring. Ideally in this case the standard is run in all the capillaries of the array.

The information on the array may be an indication that one or more capillaries are providing reduced performance. The information may be that one or more capillaries are not functioning within required parameters, for instance the capillary is too fast or too slow. The information may be a warning that performance of one or more capillaries is approaching the limit of required parameters for proper operation, preferably the warning is provided before the parameters are crossed and ideally in time to allow array replacement before the parameter are crossed. Preferably the information results in the change of the array.

According to an eighth aspect of the invention we provide a method of analysing DNA containing samples using capillary gel arrays in which the capillary gel array performs, on a plurality of occasions, a size based separation on an unknown sample in one or more capillaries and a size based separation on a standard in one or more other capillaries, the results of the one or more unknown samples being compared with the results from the one or more standards to provide the analysis results, and in which variation in a characteristic of the standard results is considered with time and variation of that characteristic outside a predetermined position provides information on the array.

The eighth aspect of the invention may include any of the features, options or possibilities set out elsewhere in this document, with particular reference to those set out in the seventh aspect of the invention and related statements.

According to a ninth aspect of the invention we provide a method of analysis DNA in a sample using a capillary gel array, in use the capillary gel array performing a size based separation on an unknown sample in one or more capillaries and a size based separation on a standard in a number of other capillaries, the results of the one or more unknown samples being compared with the results from the one or more standards to obtain the analysis results, in which between 3 and 8 of the capillaries are provided with the standard.

Preferably between 3 and 6, more preferably 4 or 5 and ideally 4 of the capillaries are provided with the standard.

The standard may include the locus HUMFIBRA.

The capillary array may include 96 capillaries.

The ninth aspect of the invention may include any of the features, options or possibilities set out elsewhere in this document.

The first and/or second and/or third and/or fourth and/or fifth and/or sixth and/or seventh and/or eighth and/or ninth aspects of the invention may include any of the features, options or possibilities set out elsewhere in this document including the following.

The capillary gel array preferably provides at least 10 capillaries, more preferably at least 25, still more preferably at least 36 capillaries and ideally in excess of 50, for instance at least 86 capillaries.

The array preferably includes a series of capillaries provided with gel. The capillaries are preferably parallel to one another. The capillaries may be arranged in a linear array.

The analysis use preferably involves analysing one or more unknown samples. Preferably a different sample is analysed in each capillary not provided with the standard. The unknown sample may be provided to the capillary along with a second standard in one or more, and preferably all cases. The second standard may be formed of a series of concatamers of known size, ideally dye labelled, for instance with a red dye.

The size based separation is preferably achieved by electrophoresis.

The standard is preferably an allelic ladder. The standard is preferably formed of a series allelic fragments. Preferably the standard includes a number of fragments relating to at least some of the variations possible at each of the loci under consideration. The loci may be as set out below.

The comparison of the unknown sample results and the standard results may involve deciding that a component of the unknown sample is equivalent in identity to a component of the standard where the unknown component position is within a positional range relative to the component of the standard. The positional range may be +/−0.5 bases. Preferably the comparison between unknown sample and standard id performed for each component.

The analysis results may be used as, or as part of, a DNA profile of the sample. The profile may thus be related to an item and/or location and/or individual. The profile may be used to link and/or exclude the sample with another sample or profile arising therefrom.

Various embodiments of the invention will now be described by way of example only and with reference to the accompanying drawings, in which.

Figure 5A:
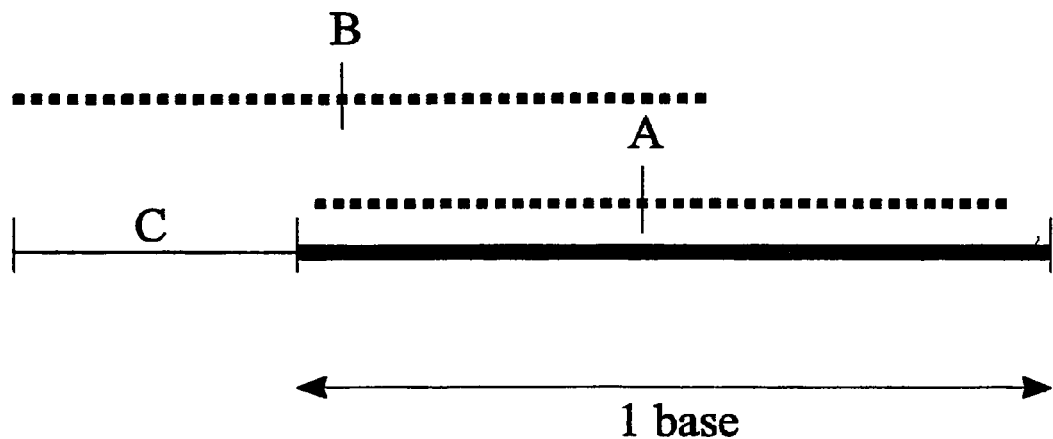
Figure 5B:
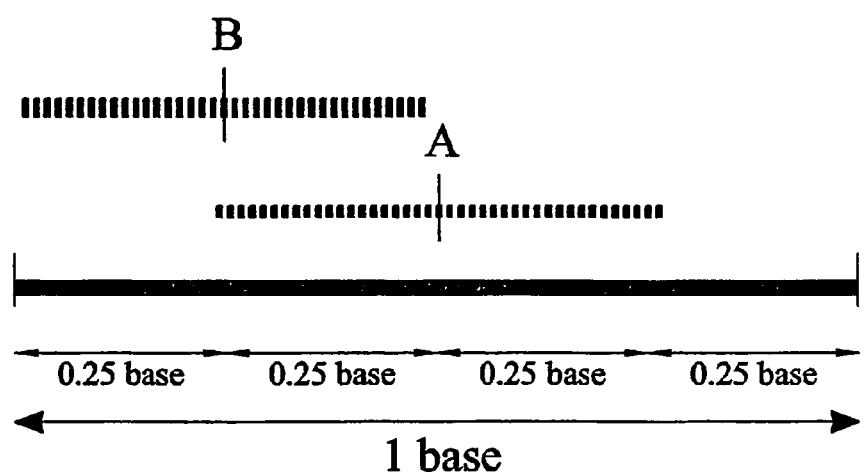
Figure 6:
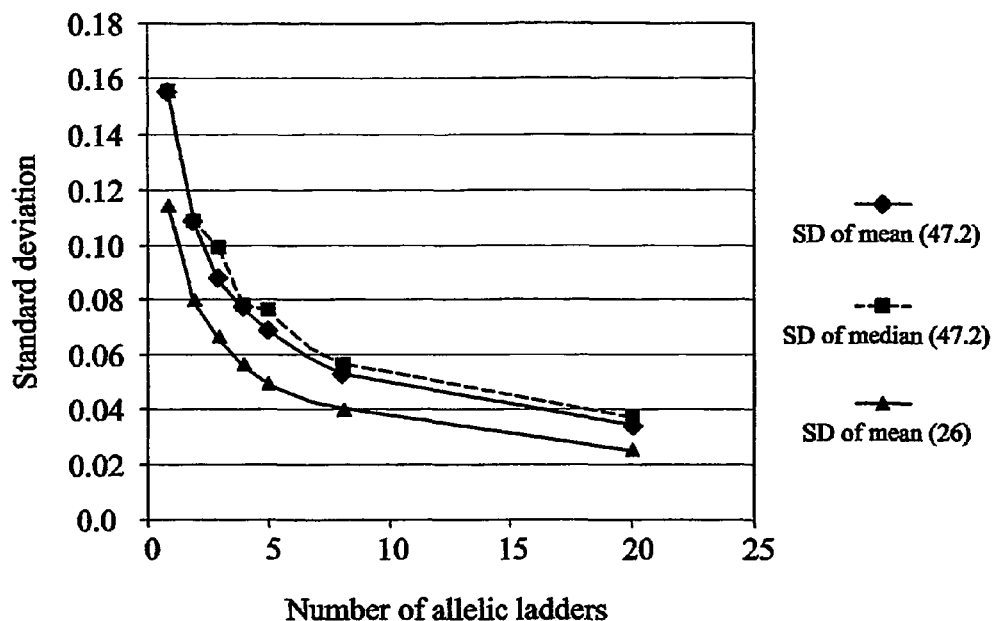
Figure 7:
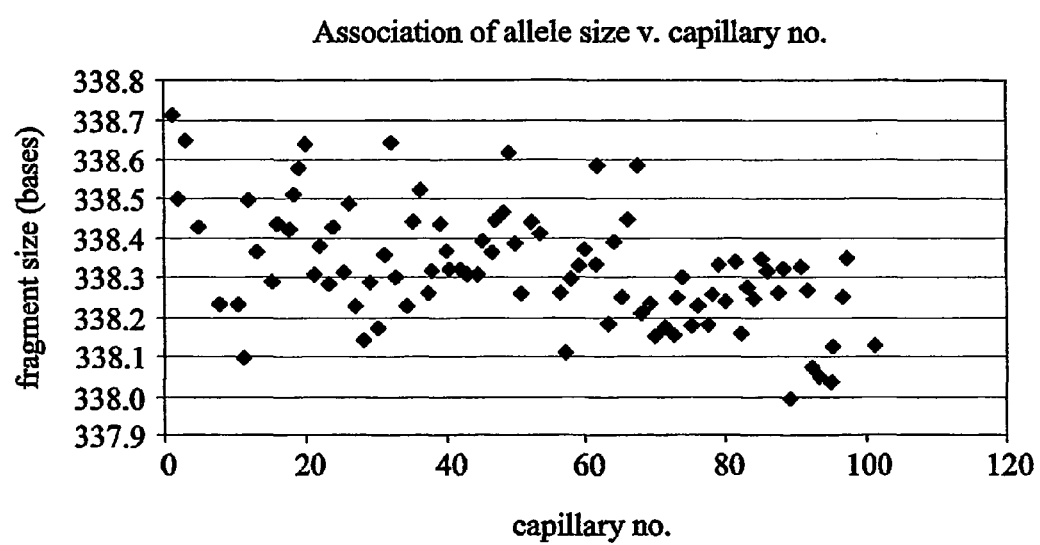

FIG. 4 presents Table 1 which is a comparison of standard deviations for HUMFIBRA alleles across five different arrays;

FIG. 5a illustrates that the error distribution of an allele can occupy a maximum one dimensional space or bin of 1 base, where A is the actual mean and B is the estimate of the mean, but that if the estimate of A is skewed then the 1-base bins may overlap and therefore there is an increased chance of the band falling into the wrong (adjacent) bin;

FIG. 5b illustrates that if the error distribution is a range of just 0.5 base then any estimate B will be within range of a 1 base bin defined by A;

FIG. 6 illustrates the standard deviation of the mean and median estimates relative to the number of allelic ladders run across a 96× capillary array for ladder markers HUMFIBRA in respect of alleles 26 and 47.2; and FIG. 7 illustrates the fragment size determined for fragments HUMFIBRA allele 47.2 relative to the capillary no. recorded from left to right facing an instrument and hence the variation in migration speed as the samples are the same in each capillary.

BACKGROUND

In forensic science, short tandem repeat analysis, is frequently used to profile an individual and/or sample from a location or an item with a view to marching that profile to another or to determining a non-match so as to eliminate a link. Applied Biosystems AMPFISTR SGM PLUS system DNA profiling technique, for instance, is a single multiplex reaction used to PCR amplify ten STR's and amelogenin (for gender determination) using fluorescent labeled primers. The discriminating power in forensic applications using such multiplexes is such that the chances of two unrelated people having the same profile is approximately $10^{-13}$.

The analysis involves collection and preparation of the sample, PCR amplification using the multiplex and separation of the products according to their size using one of a number of techniques. Separation using capillary gel array electrophoresis, CE, is becoming increasingly popular due to its ability to analysis a large number of samples in a short time period, the removal of the need to manually produce the gel and in a manner suited to automation.

The multiplexes used are designed so that the alleles of different loci which are labelled with the same colour dye do not overlap with one another so that each STR can be determined by its position and colour. The size fragments in the above example range from 100 to 360 bases and four different coloured dyes are used.

As well as the dyes associated with the multiplex products, a red labelled standard size marker having bases ranging from 50 to 400 is provided. This is formed of concatamers with constant ACTG proportions, and is run in the same lanes/capillaries as the samples being considered.

Comparison of the position of the sample products, Q samples, with the standard size marker forms the first part of the sizing process. The second part involves comparison with an allelic ladder formed of dye labelled known size and sequence fragments. The limited number of suitable dyes means that the allelic ladder has to be run in a separate lane, or in the case of CE, separate capillary, to a Q sample.

Theory of Size Determination

Both the allelic ladder markers and unknown or questioned (Q) alleles are sized relative to an internal set of DNA markers such as HD-400 ROX standards. The size of an allele (in bases) is always estimated relative to sequenced standards that comprise control allelic ladder markers.

Because all size measurements are made relative to the allelic ladder, determination of the absolute size is not important since comparisons are made directly against a control of the same size and sequence—hence it is only the distance of separation between control allelic ladder marker and the Q allele that is important. This is an important consideration because different internal size standards from different manufacturers will give different absolute results. Consequently, it is only necessary to standardise allelic ladders.

Figure 1:
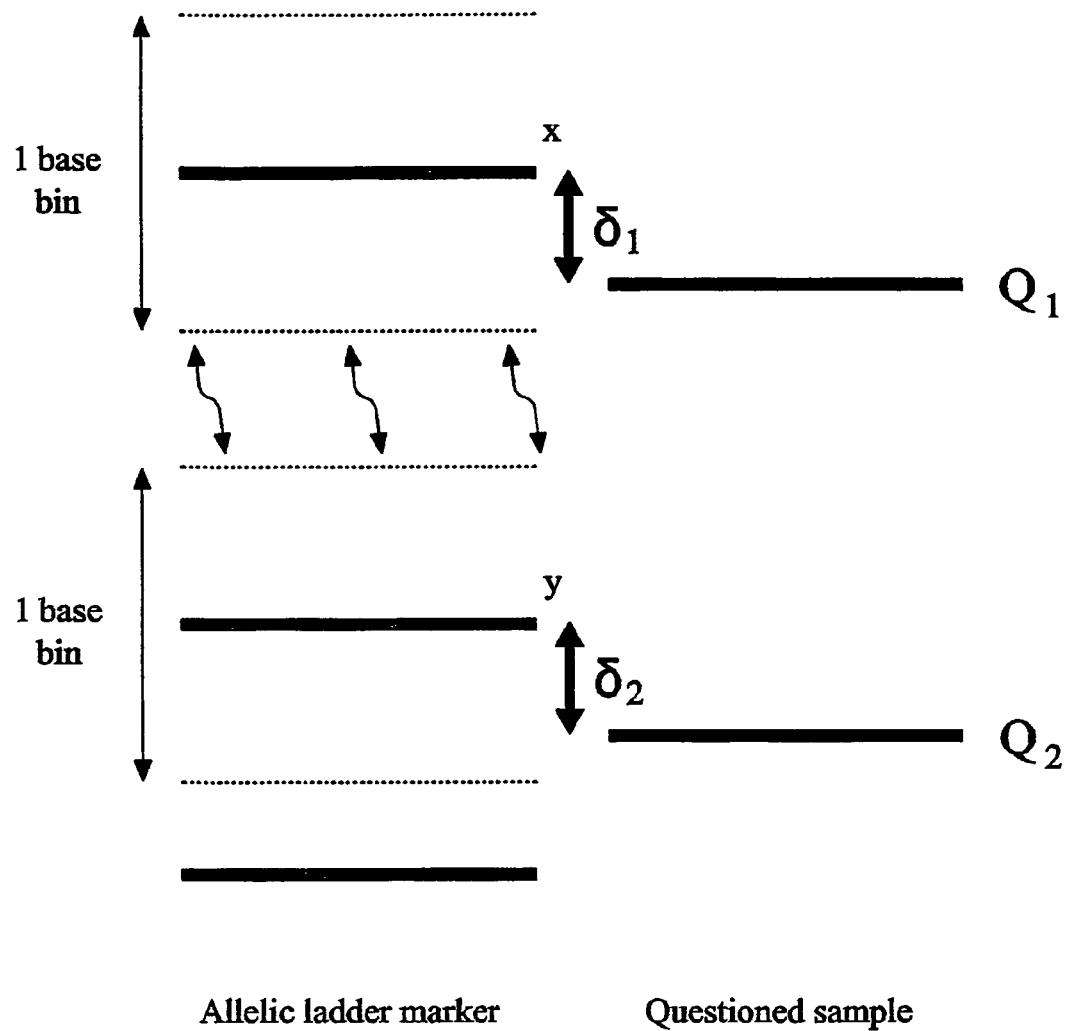
FIG. 1 shows a comparison of allelic ladder marker with questioned sample.

Provided that the size of an allele is no more than 0.5 bases from the measured allelic ladder control standard then a designation is safe to make. In any electrophoretic system distortion of the run may also occur and this can result in band shift which occasionally pushes a band into the next 'bin'. To capture these events, Gill et al [*Int. J. Legal Med.* 1996, 109, 14-22] also introduced a series of rules based on measurement of band shift relative to the allelic ladder marker which are explained with reference to FIG. 1. In particular:

a) The sizes in bases of questioned allele $Q_1$ and allelic ladder allele (x) are measured relative to the internal standard, usually by using the Elder and Southern [*Anal. Biochen:.* 1983, 128, 227-231] local method of measurement. This method calculates the size of the Q allele relative to the two adjacent internal size standards either side of it. Measurements are repeated with $Q_2$ and allelic ladder allele)). Delta (d) values are always conditioned on the allele where both the allelic ladder marker and Q alleles are coincident within the same 1 base bin. The difference in sizes of the questioned and allelic ladder markers are defined as:

$d_1|x=fQ_1-fx$ and $d_2|y=fQ_2-fy$ where $f$=size in bases.

Hence $d_1|x$ and $d_2|y$ must always be less than ±0.5 bases in order to be designated.

b) The band shift association rule states that if one band of a heterozygote is shifted, then the other allele will also be shifted in the same direction and to the same extent. If $d_1$ and $d_2$ are the respective band shifts for heterozygous alleles $Q_1$ and $Q_2$ relative to allelic ladder markers x and y respectively then the allele designation is made only if $$d_1|x-d_2|y<0.5$$

c) If a heterozygote comprising 2 rare alleles is observed, then this observation must be confirmed by re-analysis (band shifts will usually shunt the alleles into adjacent bins corresponding to alleles (x±1 and y±1) that are usually occupied by alleles that are rare. These rules can be programmed into expert systems.

Problems

In flat bed gel electrophoresis a single allelic ladder lane is used for a gel slab which may have a large number of Q sample lanes run on it. In CE the convention is also to run one capillary of the array with an allelic ladder and the other capillaries with Q samples to maximise the number of Q samples which can be processed in a given time. The applicant has determined that this approach is not appropriate for the results to be of the utmost validity.

Because it is not possible to include internal allelic ladder markers within each capillary (because of insufficient dyes and cost) the comparisons of the allelic ladder with Q samples are always made between different gels in CE. In effect each capillary is a different gel. As a result the applicant has realised that the impact of the present system of using only one allelic ladder in a set of 96 capillaries can lead to substantial question marks over the designations applied to individual results from the 95 capillaries containing samples under analysis. A methodology has therefore been developed to establish the number of allelic ladder containing capillaries which should be run to ensure that the designations are correct in an absolute sense and also to give confidence that the designations offer the necessary level of statistical confidence when scrutinised as forensic evidence, in a court of law for instance. Even with relatively small numbers of capillaries in the array, such as 16, the necessary number of allelic ladder containing capillaries needs to be verified.

Deviations in performance between one capillary and another arise for a variety of reasons.

Silica capillaries possess an excess of negative charge on their surfaces. Cations from aqueous solution build up at these surfaces, and when a charge is applied the cations, in the solution, are attracted toward the cathode. This results in a bulk flow toward the cathode, which is against the migration of the DNA, causing disruption to separation and consequent reduction of resolution of DNA fragments. The commonest method to reduce EOF is to coat the capillary inner-surface in order to modify or mask the charge on the silica surface, but the can be variations in the modification which results. Variations in the level of modification also apply to more sophisticated systems such as AB's use of a "dynamic coating polymer" POP-6 (Performance Optimised Polymer) Because the separation of the molecules, whether it be due to the transient entanglement mechanism and/or by non-tangling collisions between the DNA and polymer, is proportional to the size of the molecule, and because the mobility of DNA is also sequence dependent (notably, AT—rich sequences show anomalous migration rates relative to internal size standards) it is recommenced that the evaluation of the number of allelic ladders required is conducted in relation to the loci showing the greatest standard deviation against the size standards in test. The philosophy is preferably to carry out evaluation on worst case scenarios. Using this principal the methods and logic described should be applicable to any capillary array system whatever the number of capillaries or loci being considered apply.

Experimental Demonstration of Variation

The methodology followed in analysing the samples and obtaining standard deviation data is set out in Appendix 1 below.

Figure 2:
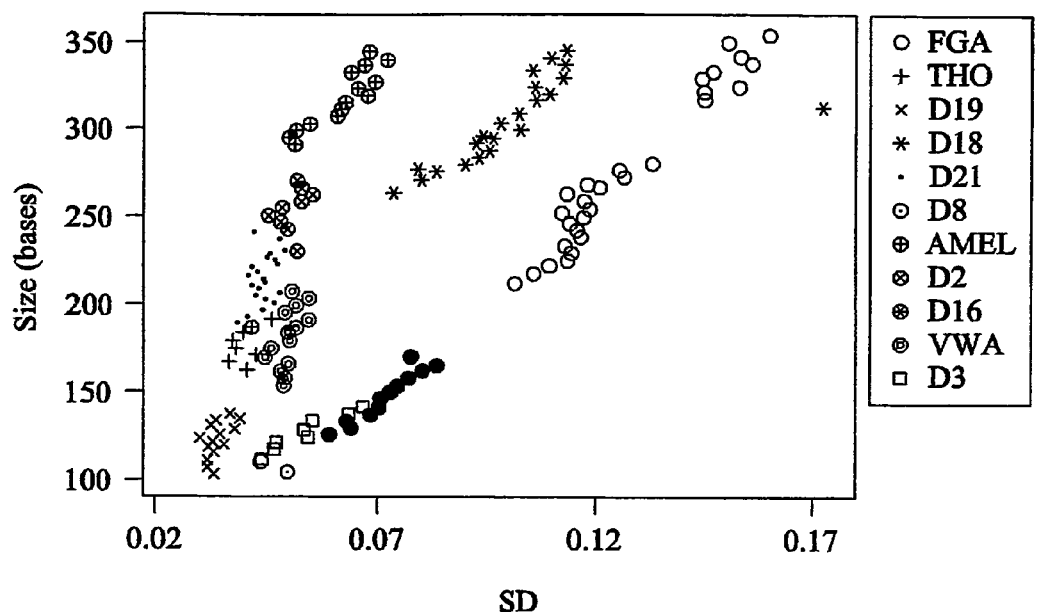
FIG. 2 is a plot of standard deviation across a 96× capillary array against size of allelic ladder markers (the loci are abbreviated as follows: D21S11 and HUMFIBRA, HUMTH01, D19S433, D18S51, D21S11, D8S1179, Amelogenin, D2S1338, D16S539, HUMVWFA31, D3S1358)

Allelic ladders were run across an entire 96× array and the standard deviations (SD's) of each allele were compared, FIG. 2. Interestingly, different loci have different characteristics. The standard deviation is both locus dependent and dependent upon the molecular weight of individual alleles; the standard deviation increases with the molecular weight. The data form three distinct clusters a) low SD: D2S1338, D16S359, D21S11, HUMVWFA31/A, HUMTH01, D19S433 b) High SD: HUMFIBRA(FGA), D8S1179, D3S1358; c) intermediate SD: D18S51. The high molecular weight alleles of the HUMFIBRA locus show the greatest SD, followed by D18S51. All other loci have much lower SD's.

The repeating sequences of the high SD loci HUMFIBRA, D8 and D3 are approximately 75% AT-rich. D18S51, which also has an elevated standard deviation, is 75% AT-rich. The only locus that does not fit this pattern is D16, which is part of the low SD cluster.

Figure 3:
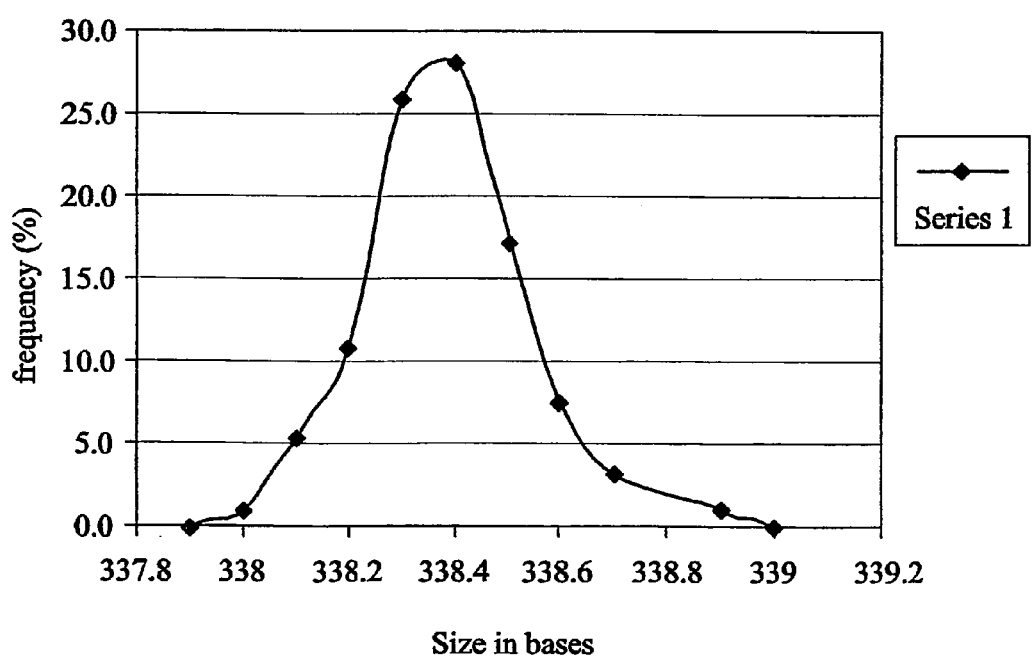
FIG. 3 illustrates a typical frequency distribution for allele size measured for HUMFIBRA 47.2 across 96 capillaries.

Worst case scenarios are defined as alleles that are most likely to fall outside their 1-base bin (as discussed in the theory of size analysis above) and these can be evaluated using high molecular weight HUMFIBRA alleles because they have the highest SD's—the range for a high molecular weight HUMFIBRA allele was approximately 1.25 bases, see FIG. 3, with a maximum SD of 0.16, see FIG. 4 which provides Table 1.

Determination of Number of Allelic Ladders Needed

Referring to the sizing theory, a 'bin' of ±0.5 bases is constructed around the observed position of an allelic ladder allele. Supposing that the range of measurement error is also one base then provided that Q alleles fall within this bin then they are correctly designated. However, this will be entirely dependent upon the measurements of the estimate of the mean (B) being coincident with the actual mean (A).

However, if the bin has been constructed from an observation (B) that is in the tail of the error distribution, see FIG. 5a, then the one base bin construct will overlap into an adjacent bin, (portion C) and it is possible therefore that Q alleles that actually should be designated in the next bin could appear to fall in the bin constructed around observation (B) and could be mis-designated as a result.

However, if the maximum measurement error range is set at just ±0.25 bases, centred on the estimate of the mean (B), see FIG. 5b, then even if the estimate (B) is taken from the tail of the measurement error distribution of (A) the Q alleles will always fall within the correct bin because the ±0.25 bases bin around (B) will always be within the ±0.5 bases bin around (A). This means that effectively, the range should be no greater than 0.5 bases in total if mis-designation is to be avoided completely.

Against this position the possibility of error is therefore minimised by providing a best estimate of the mean (B) and this is dependent upon the number of allelic ladders that are run across the 96× array in order to make such estimates. The present position in the prior art is that a single run of the allelic ladder is used to determine (B). Of course the more capillaries which are used for allelic ladders the better the estimate of (B), but the more allelic ladders that are used, the lower the number of samples that remain for analysis.

As a consequence of this position it is necessary to establish the minimum number of capillaries which need to be used for allelic ladders to achieve the necessary degree of confidence. To achieve this simulation was used to determine the relationship between the standard deviation and the number of allelic ladders run across the array. For each simulation a constant in allelic ladders were chosen at random, with replacement, from the array of 96 capillaries (where n=1 to 20) and the experiment was repeated 1000 times so that a large sample of estimates of the mean and median were generated from a single array data-set. The whole simulation was repeated by changing the value of it. Standard deviations were calculated from the 1000 estimates of the mean and median for each value on n.

The worst case scenario was evaluated specifically with the high molecular weight HUMFIBRA allele 47.2 (MW=328). Ideally, as identified above, the range should be less than 0.5 bases and this corresponds to a critical SD<0.083 (the critical SD is 0.5/6—under the assumption that with a normal distribution 99% of observations should be covered in a bin of width 6×SD). Standard deviations of means and medians from the 1000 simulations are shown in FIG. 4. As can be seen from FIG. 4, the critical standard deviation corresponded to that calculated from 4 allelic ladders for this high molecular weight allele. Standard deviations of the mean were marginally lower than standard deviations of the median estimate. The simulation experiments were repeated with allele HUMFIBRA 26 (molecular weight 253). The critical SD was achieved with just 2 allelic ladders with this lower molecular weight allele marker, see FIG. 6.

Similar determinations of the minimum number of alleles needed can be made for different loci, for different particular alleles or for different levels of certainty. The determination can also be made for different assumed distributions of the mean, other than normal. The determination can be made in a similar way also for capillary arrays with different numbers of capillaries.

Array and Capillary Specific Variations

The investigations behind this work also established that other variations in the capillary array could make a significant impact on the accuracy and/or robustness of the determinations made from the results.

When the differences in five consecutive runs were compared for HUMFIBRA 47.2 it was noted that there were a number of consistent behaviours in terms of speed of migration. As far as the 12 capillaries where fragments migrated the fastest in these tests were concerned it was notable that capillary no. 1 (the left hand capillary when viewed from the front) always migrated the fastest. Capillaries 2, 3 and 4 where also included in the list, reinforcing the trend that the capillaries that migrated the fastest were those that are low number. However, it is noticeable that fragments in capillaries 55, 62, 67 also migrated faster than expected from the trend and furthermore that this was a reproducible effect between different runs on the same array. This effect was not reproducible when a new capillary array was implemented, however, and so each array requires separate evaluation for the faster or slower mid array capillaries. The higher number capillaries, however, where consistently among the slower.

The implication of this position is that the systematic variation in speed across the array points towards the slower and faster capillaries being avoided for use as the allelic ladder bearing capillaries. This means that care needs to be taken in the choice of capillaries used to run the allelic ladders. If capillaries are all chosen from either extreme—capillaries 1-10 or 86-96 then the calculated means will tend to be continually over or underestimated. Ideally, ladders should be chosen from the mid positions on the array, subject to the further observations made below, to reduce further the chance of a mis-designating alleles. Assessment of each CE machine is advisable to establish variations of this type.

Referring to FIG. 7 it is clear that within a particular array that different capillaries will give different individual performance, over and above any effect of the left to right/fast to slow variation. Capillaries which give fast or slow speeds from the middle part of the array should also be avoided, therefore, for the allele ladder capillaries. As these performance variations effect different capillaries n different arrays it is recommenced that the set up procedure for an array include an evaluation of the speed of the individual capillaries and that the fastest few and slowest few (or those exhibiting performance above or below a threshold) being exclude for use as the allelic ladder capillaries.

To assess each machine separately and each new array separately it is recommended that each machine is characterised by running 96 allelic ladders across the array in order to characterise the separate capillaries and to ensure that those chosen to run allelic ladders give a mean result that is reasonably close to the 'true' mean.

Variation with Extent of Use

As well as inherent variation in speed for a CE machine, a CE array and individual capillaries within an array, variation with time occurs. Indeed a point is reached with Ce arrays at which one or more of the capillaries is no longer functioning and the results produced are of no use and the tests need to be repeated. Unfortunately as a significant time period often elapses between a test run being performed and the results being analysed (at which time the breakdown of the array is noticed) very substantial numbers of further tests will have been done in the meantime and these will need repeating (with consequent time and cost implications).

To avoid this the applicant suggests one or both of the following monitoring routines for CE arrays.

Firstly, by recording allelic ladder standard deviations between runs for arrays as a whole or more preferably individual capillaries the variation in the standard deviation with time can be established. SD level above a threshold can be used to warn of array breakdown and promote shifting to a new array. Secondly, a similar aim can be achieved by carrying out a full analysis by running allelic ladders across the entire array at regular intervals. The performance of an array can be monitored by direct reference to the standard deviation—it would be expected that the standard deviation would increase if the array starts to break down, acting as an early warning indicator of a problem.

The methodology set out in the present invention: in determining the effective number of allelic ladders which should be used; in determining which capillaries to avoid for the allelic ladders due to machine or array variations; in determining which capillaries to avoid for allelic ladders due to capillary specific variations; and in providing forewarning of array breakdown offers technology which provides more effective CE analysis through more rigorous results and improved processing efficiency.

Appendix 1

For sample preparation the DNA was extracted from buccal scrapes using QIAAMP spin columns (Qiagen)as described by Greensppon et al. [*J. Forensic Sci.* 1998, 43, 10-24-1030] and was PCR amplified using a STR multiplex from Applied Biosystems (AB) AMPFISTR AG Plus DNA profiling technique, as described by Cotton et al [*Forensic Sci. Int.* 2000, 112, 151-161] for use on the AB 377 flat-bed gel automated sequencer. A concatamer internal size standard AB HD400 Rox was included with every sample-this included the following fragment sizes: 50, 60, 90, 100, 120, 150, 160, 180, 190, 200, 220, 240, 260, 280, 290, 300, 320, 340, 360, 380, 400 base pairs. In addition the SGM plus allelic ladder size standard was incorporated in to 8 capillaries per array run. The allelic ladder cocktail comprises alleles from the following loci using filter F.

Dyes are 5-FAM (blue); JOE (green); NED (yellow): D3S1358 (blue); HUMVWFA31/A (blue); D16S359 (blue); D2S1338 (blue); Amelogenin (green); D8S1179 (green); D21S11 (green); D18S51 (green); D19S433 (yellow); HUMTH01 (yellow); HUMFIBRA(FGA) (yellow).

The STR loci utilised are tetrameric repeat sequences. Alleles in the ladders encompass the entire range of common alleles and are spaced at a minimum of 4 bases apart and coincide with the common alleles. In HUMFIBRA(FGA); D19S433 and D21S11 2 base variants are common; hence 2 base variants are included with the ladders for these loci.

The loading buffer (Applied Biosystems) HIDI Formamide was used.

Size Standard was diluted in HIDI Formamide at 1 in 40 ratio. 1.5 ml PCR Product+13.5 ml HIDI Formamide/HD400 Size Standard. 1.5 ml Allelic ladder+10 ml HIDI Formamide/HD400 Size Standard.

Electrophoresis was conducted on the ABI Prism 3700 CE platform using standard run parameters. Labelling and sizing of DNA fragments and their allelic designation was carried out with Genotyper 1.1.1 software.

The separation matrix used was POP-6 (Performance Optimised Polymer-6[7]) using 1×TBE running buffer (supplied by AB). The samples were injected from AB Gene Microtitre plates or ABI Thermofast Microtitre plates. A sample transfer volume of 2.5 ml using electrokinetic injection parameters of 10 kV for 11 secs, a run voltage of 7.5 kV, run temperature of 50° C.; cuvette temperature between 45° C. to 50° C. (note this temperature must be optimised for each separate 3700 machine otherwise sensitivity is compromised); the cuvette polymer flow rate is 12000 counts.

The invention claimed is:

1. A method of monitoring capillary gel array performance between two or more uses of the capillary gel array on an instrument, the method of monitoring comprising:

performing a use of the capillary gel array and performing a subsequent use of the capillary gel array, wherein a use of the capillary gel array is defined as including the capillary gel array performing a size based separation on an unknown sample in one or more capillaries, a size based separation on a second standard in those one or more capillaries and a size based separation on a first standard in one or more other different capillaries, results of the one or more unknown samples being compared with results from the one or more capillaries provided with the first standard and results of the one or more unknown samples being compared with results from the one or more capillaries provided with the second standard;

determining variation in a characteristic of the results from the capillaries provided with the first standard between two or more uses of the capillary gel array;

using variation of that characteristic outside a predetermined position to provide information on the capillary gel array, the information being that one or more of the capillaries of the array are providing reduced performance;

determining the timing of the provision of a replacement capillary gel array using the information, the capillary gel array being replaced by the replacement capillary gel array; and replacing the capillary gel array on which the use and subsequent use were performed with the replacement capillary gel array according to the timing determined.

2. A method according to claim 1 in which the standard has a migration speed or a migration distance and the performance monitored is the migration speed or migration distance of the standard in a capillary with time.

3. A method according to claim 1 in which the standard has a migration speed or a migration distance and the characteristic is the distance or speed of migration of one or more components of the standard.

4. A method according to claim 1 in which the standard has a migration speed or a migration distance or a size of component and the speed of migration and/or distance of migration and/or the size of component for one or more components of the standard is the characteristic and the characteristic is expressed as a standard deviation.

5. A method according to claim 1 in which variation is a change in the characteristic which causes the characteristic to cross a threshold.

6. A method according to claim 5 in which the threshold is an absolute value and is a preset speed or a preset distance or a preset standard deviation.

7. A method according to claim 1 in which the variation is a change in the rate of variation of the characteristic.

8. A method according to claim 1 in which the variation in the characteristic is determined after an occasion of use.

9. A method according to claim 1 in which the variation is determined from the results for the standard obtained from one or more of the capillaries of the array.

10. A method according to claim 1 in which the information on the array is an indication that one or more capillaries are not functioning within required parameters.

11. A method according to claim 1 in which the information on an array is a warning that performance of one or more capillaries is approaching the limit of required parameters for proper operation.

12. A method according to claim 1 in which the capillary gel array is also used in a method of analysing DNA containing samples, the results of the one or more unknown samples being compared with the results from the one or more capillaries provided with the standard and being compared with the second standards to provide the analysis results.

* * * * *